United States Patent [19]

Torczynski et al.

[11] Patent Number: 6,117,981
[45] Date of Patent: Sep. 12, 2000

[54] HYBRIDOMAS FOR LUNG CANCER MARKER AND MONOCLONAL ANTIBODIES THEREOF

[75] Inventors: Richard M. Torczynski, Farmers Branch; Arthur P. Bollon, Dallas, both of Tex.

[73] Assignee: Cytoclonal Pharmaceutics, Inc., Dallas, Tex.

[21] Appl. No.: 09/325,320

[22] Filed: Jun. 3, 1999

[51] Int. Cl.[7] .................. A61K 39/395; C12N 15/06; C07K 16/18; C07K 16/28; C07K 16/30
[52] U.S. Cl. .................. 530/387.7; 530/387.7; 530/387.9; 530/388.2; 530/388.8; 530/389.7; 435/326; 435/330; 435/331; 435/332; 424/138.1; 424/139.1; 424/155.1; 424/174.1
[58] Field of Search .................. 530/388.2, 388.1, 530/387.1, 350, 386, 387.7, 387.3, 387.9, 388.8, 389.7; 435/330, 328, 326, 325, 331, 332, 344; 424/138.1, 139.1, 155.1, 174.1

[56] References Cited

U.S. PATENT DOCUMENTS

| 4,737,579 | 4/1988 | Hellström et al. | 530/387 |
| 4,873,188 | 10/1989 | Hellström et al. | 435/7 |
| 4,906,562 | 3/1990 | Hellström et al. | 435/7 |
| 4,935,495 | 6/1990 | Hellström et al. | 530/387 |
| 5,091,177 | 2/1992 | Hellström et al. | 424/85.8 |
| 5,185,432 | 2/1993 | Hellström et al. | 530/388.8 |
| 5,411,884 | 5/1995 | Hellström et al. | 435/240.27 |
| 5,589,579 | 12/1996 | Torczynski et al. | 536/23.1 |
| 5,744,585 | 4/1998 | Medenica et al. | 530/388.15 |
| 5,773,579 | 6/1998 | Torczynski et al. | 530/350 |

*Primary Examiner*—Nancy A. Johnson
*Assistant Examiner*—Alana M. Harris
*Attorney, Agent, or Firm*—Sidley & Austin

[57] ABSTRACT

Hybridomas secreting monoclonal antibodies specific for an epitope found in the amino acids of LCGA associated with non-small cell lung carcinoma protein have been found. The monoclonal antibodies produced by these hybridomas can be used in in vivo and in vitro clinical diagnosis of non-small cell lung carcinoma and ovarian carcinoma and as target selective carriers for various anti-tumor agents and radio-imaging agents.

32 Claims, 1 Drawing Sheet

SEQUENCE LISTING

<160> NUMBER OF SEQ ID NOS: 2

<210> SEQ ID NO 1
<211> LENGTH: 1104
<212> TYPE: DNA
<213> ORGANISM: Homo sapiens
<220> FEATURE:
<221> NAME/KEY: CDS
<222> LOCATION: (32)..(1093)
<220> FEATURE:
<221> NAME/KEY: mat_peptide
<222> LOCATION: (119)..(1093)
<220> FEATURE:
<221> NAME/KEY: misc_feature
<222> LOCATION: (1013)..(1024)
<223> OTHER INFORMATION: phosphorylation site recognized by protein
      kinase C and other kinases

<400> SEQUENCE: 1

```
gcccgcgccc gccccgcagg agcccgcgaa g atg ccc cgg cgc agc ctg cac        52
                                   Met Pro Arg Arg Ser Leu His
                                                       -25 gcg gcg gcc gtg ctc ctg ctg gtg atc tta aag gaa cag cct tcc agc      100
Ala Ala Ala Val Leu Leu Leu Val Ile Leu Lys Glu Gln Pro Ser Ser
        -20                 -15                 -10 ccg gcc cca gtg aac ggt tcc aag tgg act tat ttt ggt cct gat ggg      148
Pro Ala Pro Val Asn Gly Ser Lys Trp Thr Tyr Phe Gly Pro Asp Gly
 -5                  -1   1                   5                  10 gag aat agc tgg tcc aag aag tac ccg tcg tgt ggg ggc ctg ctg cag      196
Glu Asn Ser Trp Ser Lys Lys Tyr Pro Ser Cys Gly Gly Leu Leu Gln
                 15                  20                  25 tcc ccc ata gac ctg cac agt gac atc ctc cag tat gac gcc agc ctc      244
Ser Pro Ile Asp Leu His Ser Asp Ile Leu Gln Tyr Asp Ala Ser Leu
             30                  35                  40 acg ccc ctc gag ttc caa ggc tac aat ctg tct gcc aac aag cag ttt      292
Thr Pro Leu Glu Phe Gln Gly Tyr Asn Leu Ser Ala Asn Lys Gln Phe
         45                  50                  55 ctc ctg acc aac aat ggc cat tca gtg aag ctg aac ctg ccc tcg gac      340
Leu Leu Thr Asn Asn Gly His Ser Val Lys Leu Asn Leu Pro Ser Asp
     60                  65                  70 atg cac atc cag ggc ctc cag tct cgc tac agt gcc acg cag ctg cac      388
Met His Ile Gln Gly Leu Gln Ser Arg Tyr Ser Ala Thr Gln Leu His
 75                  80                  85                  90 ctg cac tgg ggg aac ccg aat gac ccg cac ggc tct gag cac acc gtc      436
Leu His Trp Gly Asn Pro Asn Asp Pro His Gly Ser Glu His Thr Val
                 95                 100                 105 agc gga cag cac ttc gcc gcc gag ctg cac att gtc cat tat aac tca      484
Ser Gly Gln His Phe Ala Ala Glu Leu His Ile Val His Tyr Asn Ser
             110                 115                 120 gac ctt tat cct gac gcc agc act gcc agc aac aag tca gaa ggc ctc      532
Asp Leu Tyr Pro Asp Ala Ser Thr Ala Ser Asn Lys Ser Glu Gly Leu
         125                 130                 135 gct gtc ctg gct gtt ctc att gag atg ggc tcc ttc aat ccg tcc tat      580
Ala Val Leu Ala Val Leu Ile Glu Met Gly Ser Phe Asn Pro Ser Tyr
     140                 145                 150 gac aag atc ttc agt cac ctt caa cat gta aag tac aaa ggc cag gaa      628
Asp Lys Ile Phe Ser His Leu Gln His Val Lys Tyr Lys Gly Gln Glu
155                 160                 165                 170 gca ttc gtc ccg gga ttc aac att gaa gag ctg ctt ccg gag agg acc      676
Ala Phe Val Pro Gly Phe Asn Ile Glu Glu Leu Leu Pro Glu Arg Thr
                 175                 180                 185
```

-continued

```
gct gaa tat tac cgc tac cgg ggg tcc ctg acc aca ccc cct tgc aac      724
Ala Glu Tyr Tyr Arg Tyr Arg Gly Ser Leu Thr Thr Pro Pro Cys Asn
            190                 195                 200 ccc act gtg ctc tgg aca gtt ttc cga aac ccc gtg caa att tcc cag      772
Pro Thr Val Leu Trp Thr Val Phe Arg Asn Pro Val Gln Ile Ser Gln
            205                 210                 215 gag cag ctg ctg gct ttg gag aca gcc ctg tac tgc aca cac atg gac      820
Glu Gln Leu Leu Ala Leu Glu Thr Ala Leu Tyr Cys Thr His Met Asp
220                 225                 230 gac cct tcc ccc aga gaa atg atc aac aac ttc cgg cag gtc cag aag      868
Asp Pro Ser Pro Arg Glu Met Ile Asn Asn Phe Arg Gln Val Gln Lys
235                 240                 245                 250 ttc gat gag agg ctg gta tac acc tcc ttc tcc caa gtg caa gtc tgt      916
Phe Asp Glu Arg Leu Val Tyr Thr Ser Phe Ser Gln Val Gln Val Cys
                255                 260                 265 act gcg gca gga ctg agt ctg ggc atc atc ctc tca ctg gcc ctg gct      964
Thr Ala Ala Gly Leu Ser Leu Gly Ile Ile Leu Ser Leu Ala Leu Ala
            270                 275                 280 ggc att ctt ggc atc tgt att gtg gtg gtg gtg tcc att tgg ctt ttc     1012
Gly Ile Leu Gly Ile Cys Ile Val Val Val Val Ser Ile Trp Leu Phe
            285                 290                 295 aga agg aag agt atc aaa aaa ggt gat aac aag gga gtc att tac aag     1060
Arg Arg Lys Ser Ile Lys Lys Gly Asp Asn Lys Gly Val Ile Tyr Lys
300                 305                 310 cca gcc acc aag atg gag act gag gcc cac gct tgaggtcccc g            1104
Pro Ala Thr Lys Met Glu Thr Glu Ala His Ala
315                 320                 325

<210> SEQ ID NO 2
<211> LENGTH: 354
<212> TYPE: PRT
<213> ORGANISM: Homo sapiens

<400> SEQUENCE: 2

Met Pro Arg Arg Ser Leu His Ala Ala Ala Val Leu Leu Val Ile
                -25                 -20                 -15

Leu Lys Glu Gln Pro Ser Ser Pro Ala Pro Val Asn Gly Ser Lys Trp
            -10                  -5                  -1   1

Thr Tyr Phe Gly Pro Asp Gly Glu Asn Ser Trp Ser Lys Lys Tyr Pro
          5                  10                  15

Ser Cys Gly Gly Leu Leu Gln Ser Pro Ile Asp Leu His Ser Asp Ile
 20                  25                  30                  35

Leu Gln Tyr Asp Ala Ser Leu Thr Pro Leu Glu Phe Gln Gly Tyr Asn
                 40                  45                  50

Leu Ser Ala Asn Lys Gln Phe Leu Leu Thr Asn Asn Gly His Ser Val
             55                  60                  65

Lys Leu Asn Leu Pro Ser Asp Met His Ile Gln Gly Leu Gln Ser Arg
         70                  75                  80

Tyr Ser Ala Thr Gln Leu His Leu His Trp Gly Asn Pro Asn Asp Pro
     85                  90                  95

His Gly Ser Glu His Thr Val Ser Gly Gln His Phe Ala Ala Glu Leu
100                 105                 110                 115

His Ile Val His Tyr Asn Ser Asp Leu Tyr Pro Asp Ala Ser Thr Ala
                120                 125                 130

Ser Asn Lys Ser Glu Gly Leu Ala Val Leu Ala Val Leu Ile Glu Met
            135                 140                 145

Gly Ser Phe Asn Pro Ser Tyr Asp Lys Ile Phe Ser His Leu Gln His
150                 155                 160
```

-continued

```
Val Lys Tyr Lys Gly Gln Glu Ala Phe Val Pro Gly Phe Asn Ile Glu
    165                 170                 175

Glu Leu Leu Pro Glu Arg Thr Ala Glu Tyr Tyr Arg Tyr Arg Gly Ser
180             185                 190                 195

Leu Thr Thr Pro Pro Cys Asn Pro Thr Val Leu Trp Thr Val Phe Arg
                200                 205                 210

Asn Pro Val Gln Ile Ser Gln Glu Gln Leu Leu Ala Leu Glu Thr Ala
            215                 220                 225

Leu Tyr Cys Thr His Met Asp Asp Pro Ser Pro Arg Glu Met Ile Asn
        230                 235                 240

Asn Phe Arg Gln Val Gln Lys Phe Asp Glu Arg Leu Val Tyr Thr Ser
    245                 250                 255

Phe Ser Gln Val Gln Val Cys Thr Ala Ala Gly Leu Ser Leu Gly Ile
260             265                 270                 275

Ile Leu Ser Leu Ala Leu Ala Gly Ile Leu Gly Ile Cys Ile Val Val
                280                 285                 290

Val Val Ser Ile Trp Leu Phe Arg Arg Lys Ser Ile Lys Lys Gly Asp
            295                 300                 305

Asn Lys Gly Val Ile Tyr Lys Pro Ala Thr Lys Met Glu Thr Glu Ala
        310                 315                 320

His Ala
    325
```

HYBRIDOMAS FOR LUNG CANCER MARKER AND MONOCLONAL ANTIBODIES THEREOF

BACKGROUND OF THE INVENTION

Lung cancer is the most common form of cancer in the world. Typical diagnosis of lung cancer combines x-ray with sputum cytology. Unfortunately, by the time a patient seeks medical attention for their symptoms, the cancer is at such an advanced state it is usually incurable. Consequently, research has been focused on early detection of tumor markers before the cancer becomes clinically apparent and while the cancer is still localized and amenable to therapy.

The World Health Organization has classified lung cancer into four major histological or morphological types: (1) squamous cell carcinoma, (2) adenocarcinoma, (3) large cell carcinoma, and (4) small cell lung carcinoma. (World Health Organization. 1982. "The World Health Organization Histological Typing of Lung Tumors," *Am J Clin Pathol* 77:123–136). However, there is a great deal of tumor heterogeneity even within the various subtypes, and it is not uncommon for lung cancer to have features of more than one morphological subtype. The term "non-small cell lung carcinoma" (NSCLS) has been used to distinguish squamous carcinomas, adenocarcinomas, and large cell carcinomas from small cell lung carcinomas.

Particular interest has been given to the identification of antigens associated with lung cancer. These antigens have been used in screening, diagnosis, clinical management, and potential treatment of lung cancer. For example, carcinoembryonic antigen (CEA) has been used as a tumor marker of cancer including lung cancer. (Nutini, et al. 1990. "Serum NSE, CEA, CT, CA 15-3 levels in human lung cancer," *Int J Biol Markers* 5:198–202). Squamous cell carcinoma antigen (SCC) is another established serum marker. (Margolis, et al. 1994. "Serum tumor markers in non-small cell lung cancer," *Cancer* 73:605–609.). Other serum antigens for lung cancer include antigens recognized by monoclonal antibodies (MAb) 5E8, 5C7, and 1F10, the combination of which distinguishes between patients with lung cancer from those without. (Schepart, et al. 1988. "Monoclonal antibody-mediated detection of lung cancer antigens in serum," *Am Rev Respir Dis* 138:1434–8). Serum CA 125, initially described as an ovarian cancer-associated antigen, has been investigated for its use as a prognostic factor in NSCLC. (Diez, et al. 1994. "Prognostic significance of serum CA 125 antigen assay in patients with non-small cell lung cancer," *Cancer* 73:136876). Other tumor markers studied for utilization in multiple biomarker assays for lung cancer include carbohydrate antigen CA19-9, neuron specific enolase (NSE), tissue polypeptide antigen (TPA), alpha fetoprotein (AFP), HCG beta subunit, and LDH. (Mizushima, et al. 1990. "Clinical significance of the number of positive tumor markers in assisting the diagnosis of lung cancer with multiple tumor marker assay," *Oncology* 47:43–48; Lombardi, et al. 1990. "Clinical significance of a multiple biomarker assay in patients with lung cancer," *Chest* 97:639–644; and Buccheri, et al. 1986. "Clinical value of a multiple biomarker assay in patients with bronchogenic carcinoma," *Cancer* 57:2389–2396).

Monoclonal antibodies (MAb) to the antigens associated with lung cancer have been generated and examined as possible diagnostic and/or prognostic tools. For example, MAbs for lung cancer were first developed to distinguish non-small cell lung carcinoma (NSCLC) which includes squamous, adenocarcinoma, and large cell carcinomas from small cell lung carcinomas (SCLC). (Mulshine, et al. 1983. "Monoclonal antibodies that distinguish non-small-cell from small-cell lung cancer," *J Immunol* 121:497–502). MAbs have also been developed as immunocytochemical stains for sputum samples to predict the progression of lung cancer. (Tockman, et al. 1988. "Sensitive and specific monoclonal antibody recognition of human lung cancer antigen on preserved sputum cells: a new approach to early lung cancer detection," *J Clin Oncol* 6:1685–1693). U.S. Pat. No. 4,816,402 discloses a murine hybridoma monoclonal antibody for determining bronchopulmonary carcinomas and possibly adenocarcinomas. Other monoclonal antibodies utilized in immunohistochemical studies of lung carcinomas include MCA 44-3A6, L45, L20, SLC454, L6, and YH206. (Radosevich, et al. 1985. "Monoclonal antibody 44-3A6 as a probe for a novel antigen found on human lung carcinomas with glandular differentiation," *Cancer Res* 45:5808–5812).

Despite the numerous examples of isolated lung cancer antigens and subsequent production of MAb to these antigens, none has yet emerged that has changed clinical practice. (Mulshine, et al., "Applications of monoclonal antibodies in the treatment of solid tumors," In: *Biologic Therapy of Cancer.* Edited by V. T. Devita, S. Hellman, and S. A. Rosenberg. Philadelphia: J B Lippincott, 1991, pp. 563–588). There is a continuing need to identify specific antigens associated with lung cancer and to generate monoclonal antibodies (MAb) to these antigens for the development of tools for diagnosing cancer, targeting of drugs and other treatments to particular sites in the body, imaging of tumors for radiotherapy, and possible generating therapeutic agents for cancer.

In U.S. Pat. No. 5,589,579 and U.S. Pat. No. 5,773,579, a lung cancer marker antigen specific for non-small cell lung carcinoma was identified and designated HCAVIII. Subsequently, the antigen was renamed HCAXII and finally renamed LCGA. The antigen was found useful in methods for detection of non-small cell lung cancer and for potential production of antibodies and probes for treatment compositions. These patents include the nucleic acid sequence coding ski for the cell surface protein LCGA (HCAVIII) which is highly specific for non-small cell lung cancer cells as well as isolated proteins encoded by the nucleic acid sequences.

Three monoclonal antibodies specific for LCGA have now been found. These antibodies can be utilized for both in vivo and in vitro clinical diagnosis of non-small cell lung carcinoma and as target selective carriers for various antitumor agents and radioimaging agents.

SUMMARY OF THE INVENTION

In one aspect, the present invention is a monoclonal antibody, an antibody fragment, or a recombinant binding protein thereof which specifically binds to non-small cell lung carcinoma cell antigen LCGA and which has the epitope binding specificity of an antibody produced by the hybridoma cell line 3E10-H10-F12 designated as ATCC NO. HB-12564. A preferred embodiment is the monoclonal antibody secreted by the hybridoma cell line 3E10-H10-F12 (ATCC NO. HB-12564). Another preferred embodiment is an antigen binding fragment derived from the antibody secreted by the hybridoma cell line 3E10-H10-F12 (ATCC NO. HB-12564). Another preferred embodiment is a recombinant binding protein comprising a variable region of the monoclonal antibody secreted by the hybridoma cell line 3E10-H10-F12 (ATCC NO. HB-12564). A most preferred embodiment is a monoclonal antibody, antigen binding fragment or recombinant binding protein thereof which specifically binds to amino acids 173 through 179 of SEQ ID NO:2 or a portion thereof.

In another aspect, the present invention is a hybridoma cell line which produces a monoclonal antibody which binds to non-small cell lung carcinoma cell antigen LCGA and which has the epitope binding specificity of an antibody produced by the hybridoma cell line 3E10-H10-F12 (ATCC NO. FB-12564). A preferred embodiment is the hybridoma cell line 3E10-H10-F12 (ATCC NO. HB-12564).

In another aspect, the present invention is a composition comprising a monoclonal antibody, an antibody fragment, or a recombinant binding protein thereof which specifically binds to amino acids 173 through 179 of SEQ ID NO:2 or a portion thereof or which has the epitope binding specificity of an antibody produced by the hybridoma cell line 3E10-H10-F12 (ATCC NO. HB-12564). In a preferred embodiment, the composition comprises an isolated human monoclonal antibody which specifically binds to amino acids 173 through 179 of SEQ ID NO:2 or a portion thereof or which has the epitope binding specificity of an antibody produced by the hybridoma cell line 3E10-H10-F12 (ATCC NO. HB-12564). In another preferred embodiment, the composition comprises a humanized antibody which specifically binds to amino acids 173 through 179 of SEQ ID NO:2 or a portion thereof or which has the epitope binding specificity of an antibody produced by the hybridoma cell line 3E10-H10-F12 (ATCC NO. HB-12564).

In another aspect, the present invention is an isolated antibody which specifically binds to amino acids 173 through 179 of SEQ ID NO:2 or a portion thereof or which has the epitope binding specificity of an antibody produced by the hybridoma cell line 3E10-H10-F12 (ATCC NO. HB-12564).

In another aspect, the present invention is a method of detecting LCGA in a patient sample by first contacting the patient sample with an effective amount of monoclonal antibody, antigen binding fragment or recombinant binding protein thereof which specifically binds to LCGA and which has the epitope binding specificity of an antibody produced by the hybridoma cell line 3E10-H10-F12 (ATCC NO. HB-12564), then allowing the antibody, antigen binding fragment or recombinant binding protein thereof to bind to the epitope to form a bound complex, and finally quantitating the bound complex and equating the presence of the bound complex with the presence of LCGA in the sample, thus indicating the presence of non-small cell lung carcinoma.

In another aspect, the present invention is a method of detecting ovarian cancer in a patient sample by first contacting the patient ovarian tissue sample with an effective amount of monoclonal antibody, antigen binding fragment or recombinant binding protein thereof which has the epitope binding specificity of an antibody produced by the hybridoma cell line 3E10-H10-F12 (ATCC NO. HB-12564), then allowing the antibody, antigen binding fragment or recombinant binding protein thereof to bind to the epitope to form a bound complex, and finally quantitating the bound complex and equating the presence of the bound complex with the presence of ovarian carcinoma cells in the sample.

In another aspect, the present invention is a monoclonal antibody, antigen binding fragment or recombinant binding protein thereof which binds to non-small cell lung carcinoma cell antigen LCGA and which has the epitope binding specificity of an antibody produced by hybridoma cell line 6F11-F8-C11 designated as ATCC NO. HB-12565. A preferred embodiment is the monoclonal antibody secreted by the hybridoma cell line 6F11-F8-C11 (ATCC NO. HB-12565). Another preferred embodiment is an antigen binding fragment derived from the antibody secreted by the hybridoma cell line 6F11-F8-C11 (ATCC NO. HB-12565). Another preferred embodiment is a recombinant binding protein comprising a variable region of the monoclonal antibody secreted by the hybridoma cell line 6F11-F8-C11 (ATCC NO. HB-12565). A most preferred embodiment is a monoclonal antibody, antigen binding fragment or recombinant binding protein thereof which specifically binds to amino acids 209 through 215 of SEQ ID NO:2 or a portion thereof.

In another aspect, the present invention is a hybridoma cell line which produces a monoclonal antibody which binds to non-small cell lung carcinoma cell antigen LCGA and which has the epitope binding specificity of an antibody produced by the hybridoma cell line 6F11-F8-C11 (ATCC NO. HB-12565). A preferred embodiment is the hybridoma cell line 6F11-F8-C11 (ATCC NO. HB-12565).

In another aspect, the present invention is a composition comprising a monoclonal antibody, an antibody fragment, or a recombinant binding protein thereof which specifically binds to amino acids 209 through 215 of SEQ ID NO:2 or a portion thereof or which has the epitope binding specificity of an antibody produced by the hybridoma cell line 6F11-F8-C11 (ATCC NO. HB-12565). In a preferred embodiment, the composition comprises an isolated human monoclonal antibody which specifically binds to amino acids 209 through 215 of SEQ ID NO:2 or a portion thereof or which has the epitope binding specificity of an antibody produced by the hybridoma cell line 6F11-F8-C11 (ATCC NO. HB-12565). In another preferred embodiment, the composition comprises a humanized antibody which specifically binds to amino acids 209 through 215 of SEQ ID NO:2 or a portion thereof or which has the epitope binding specificity of an antibody produced by the hybridoma cell line 6F11-F8-C11 (ATCC NO. HB-12565).

In another aspect, the present invention is an isolated antibody which specifically binds to amino acids 209 through 215 of SEQ ID NO:2 or a portion thereof or which has the epitope binding specificity of an antibody produced by the hybridoma cell line 6F11-F8-C11 (ATCC NO. HB-12565).

In another aspect, the present invention is a method of detecting LCGA in a patient sample by first contacting the patient sample with an effective amount of monoclonal antibody, antigen binding fragment or recombinant binding protein thereof which specifically binds to LCGA and which has the epitope binding specificity of an antibody produced by the hybridoma cell line 6F11-F8-C11 (ATCC NO. HB-12565), then allowing the antibody, antigen binding fragment or recombinant binding protein thereof to bind to the epitope to form a bound complex, and finally quantitating the bound complex and equating the presence of the bound complex with the presence of LCGA in the sample, thus indicating the presence of non-small cell lung carcinoma.

In another aspect, the present invention is a method of detecting ovarian carcinoma in a patient sample by first contacting the patient sample with an effective amount of monoclonal antibody, antigen binding fragment or recombinant binding protein thereof which has the epitope binding specificity of an antibody produced by the hybridoma cell line 6F11-F8-C11 (ATCC NO. HB-12565), then allowing the antibody, antigen binding fragment or recombinant binding protein thereof to bind to the epitope to form a bound complex, and finally quantitating the bound complex and equating the presence of the bound complex with the presence of ovarian carcinoma cells in the sample.

In yet another aspect, the present invention is a monoclonal antibody, antigen binding fragment or recombinant binding protein thereof which binds to non-small cell lung carcinoma cell antigen LCGA and which has the epitope binding specificity of an antibody produced by the hybridoma cell line 3C2-E7-F10 designated as ATCC NO. HB-12566. A preferred embodiment is the monoclonal antibody secreted by the hybridoma cell line 3C2-E7-F10 (ATCC NO. HB-12566). Another preferred embodiment is an antigen binding fragment derived from the antibody secreted by the hybridoma cell line 3C2-E7-F10 (ATCC NO. HB-12566). Another preferred embodiment is a recombinant binding protein comprising a variable region of the monoclonal antibody secreted by the hybridoma cell line 3C2-E7-F10 (ATCC NO. HB-12566).

In another aspect, the present invention is a hybridoma cell line which produces a monoclonal antibody which binds to non-small cell lung carcinoma cell antigen LCGA and which has the epitope binding specificity of an antibody produced by the hybridoma cell line 3C2-E7-F10 (ATCC NO. HB-12566). A preferred embodiment is the hybridoma cell line 3C2-E7-F10 (ATCC NO. HB-12566).

In another aspect, the present invention is a composition comprising a monoclonal antibody, an antibody fragment, or a recombinant binding protein thereof which has the epitope binding specificity of an antibody produced by the hybridoma cell line 3C2-E7-F10 (ATCC NO. HB-12566). In a preferred embodiment, the composition comprises an isolated human monoclonal antibody which has the epitope binding specificity of an antibody produced by the hybridoma cell line 3C2-E7-F10 (ATCC NO. HB-12566). In another preferred embodiment, the composition comprises a humanized antibody which has the epitope binding specificity of an antibody produced by the hybridoma cell line 3C2-E7-F10 (ATCC NO. HB-12566).

In another aspect, the present invention is an isolated antibody which has the epitope binding specificity of an antibody produced by the hybridoma cell line 3C2-E7-F10 (ATCC NO. HB-12566).

In another aspect, the present invention is a method of detecting LCGA in a patient sample by first contacting the patient sample with an effective amount of monoclonal antibody, an antibody fragment, or a recombinant binding protein thereof which specifically binds to LCGA and which has the epitope binding specificity of an antibody produced by the hybridoma cell line 3C2-E7-F10 (ATCC NO. HB-12566), then allowing the monoclonal antibody, an antibody fragment, or a recombinant binding protein thereof to bind to LCGA to form a bound complex, and finally quantitating the bound complex and equating the presence of the bound complex with the presence of LCGA in the sample, thus indicating the presence of non-small cell lung carcinoma.

In another aspect, the present invention is a method of detecting ovarian carcinoma in a patient sample by first contacting the patient sample with an effective amount of monoclonal antibody, an antibody fragment, or a recombinant binding protein thereof which has the epitope binding specificity of an antibody produced by the hybridoma cell line 3C2-E7-F10 (ATCC NO. HB-12566), then allowing the monoclonal antibody, an antibody fragment, or a recombinant binding protein thereof to bind to the tissue to form a bound complex, and finally quantitating the bound complex and equating the presence of the bound complex with the presence of ovarian carcinoma cells in the sample.

DETAILED DESCRIPTION OF THE INVENTION

The present invention provides hybridomas secreting monoclonal antibodies (MAb) specific for a epitoped found in the amino acids of LCGA.

As used herein, an antibody is said to "bind" a molecule if it is capable of specifically reacting with the molecule to thereby bind the molecule to the antibody. The term "epitope" refers to that portion of a molecule which can be recognized and bound by an antibody. "Antigen" is a molecule which can be recognized and bound by an antibody, and is capable of inducing an animal to produce an antibody capable of binding to an epitope of that antigen. The term "antibody" or "monoclonal antibody" (MAb) is used herein to include intact molecules as well as fragments thereof which are capable of binding to an epitope.

The antibodies of the present invention are monoclonal antibodies or fragments thereof capable of binding to epitopes on LCGA. Such monoclonal antibodies can be prepared using hybridoma technology. (Harlow, et al., *Antibodies: A Laboratory Manual,* Cold Spring Harbor Laboratories, New York, 1988, incorporated herein by reference). In general, such procedures involved immunizing an animal, preferably a mouse, with LCGA. Initially, a group of mice were immunized with about 50 micrograms of LCGA (amino acids -1 to 274 of SEQ ID NO:2) emulsified in Freund's complete adjuvant. At three week intervals, the mice were immunized with about 50 micrograms LCGA emulsified with Freund's incomplete adjuvant. Ten days following the third immunization, serum samples were taken from the mice, and the relative serum antibody titers to LCGA were determined by a solid phase enzyme linked immunosorbent assay (ELISA). If the serum antibody titers were low, three-week boosters were repeated until an adequate antibody titer was established. Mice exhibiting elevated serum antibody titers were subjected to a final regimen of intravenous LCGA injections over a period of three days. Spleens from these mice were then used in the fusions.

Spleens from the immunized mice were excised and physically disrupted, and the immune splenocytes were collected. A polyethylene glycol-mediated fusion was performed using the splenocytes and Balb/c-derived HGPRT (hypoxanthine guanine phosphoribosyl transferase) deficient P3x63Ag8.653 plasmacytoma cells. The fused cells were plated onto several 96-well plates and the resultant hybridomas were identified by selection in tissue culture medium containing hypoxanthine, aminopterin, and thymidine (HAT) medium for approximately two to three weeks.

The hybridoma cells obtained through such selection were then assayed to identify clones which secrete antibodies capable of binding to LCGA. It will be appreciated that fragments of the antibody of the present invention can be used according to the methods disclosed herein for the detection and treatment of non-small cell lung carcinoma in the same manner as the intact antibody. Such fragments are typically produced by proteolytic cleavage, using enzymes such as papain or pepsin. Alternatively, epitope binding fragments can be produced through the application of the recombinant DNA technology or through synthetic chemistry.

Preferred cell lines obtainable through the methods of the present invention are those which produce antibodies capable of binding to LCGA present on non-small cell lung carcinoma cells. Most preferred cell lines of the present invention include the monoclonal antibody-producing cell line 3E10- H10-F12 deposited under the provisions of the Budapest Treaty with the American Type Culture Collection (ATCC), 10801 University Boulevard, Manassas, Va. 20110-2209 on Sep. 11, 1998, given the ATCC designation HB-12564. A second preferred cell line is 6F11-F8-C11 deposited with ATCC on Sep. 11, 1998, identified as HB-12565. A third preferred cell line is 3C2-E-7-F10 deposited with ATCC on Sep. 11, 1998, designated ATCC HB-12566. The preferred medium for maintaining the hybridomas of the present invention consists of the following ingredients at the specified final concentration: CPSP-3 (Sigma Chemical Co, St. Louis, Mo.), 10%; sodium pyruvate (Sigma), 1 mM; L-glutamine (BioWhittaker, Inc., Walkersville, Md.), 2 mM; gentamycin (BioWittaker), 50 $\mu$M; Origen (Fisher Scientific, Pittsburgh, Pa.), 5%; 2-mercaptoethanol (Sigma), 0.05 mM; and RPMI 1640 (BioWhittaker), 85%. The monoclonal antibodies of the present invention are of the $IgG_1$ class.

The monoclonal antibodies of the present invention specifically bind to the cell surface glycoprotein antigen LCGA associated with non-small cell lung carcinoma (NSCLC). SEQ ID NO:1 represents the cDNA encoding LCGA and a presumed signal peptide. SEQ ID NO:2 represents the signal peptide (amino acid residues −29 to −1) followed by the mature protein (amino acid residues 1 to 325). The hybridoma cell lines of the present invention secrete monoclonal antibodies (MAb) which specifically bind to epitopes of LCGA (SEQ ID NO:2). It is understood that the monoclonal antibodies produced by the hybridoma cell lines of the present invention specifically bind to one or more epitopes of LCGA. For example, one such cell line is 3E10-H10-F12, deposit designation ATCC HB-12564, that produces a monoclonal antibody which has been shown to specifically bind to a region of LCGA comprising amino acids 173–179 of SEQ ID NO:2 or a portion thereof. Another cell line is 6F11-F8-C11, deposit designation ATCC HB-12565, that produces a monoclonal antibody which has demonstrated specific binding to a region of LCGA comprising amino acids 209–215 of SEQ ID NO:2 or a portion thereof. A third cell line 3C2-E7-F10, deposit designation ATCC HB-12566 also produces a monoclonal antibody which specifically binds to LCGA.

To demonstrate the specificity of the monoclonal antibodies of the present invention against LCGA, selected cancer cell lines were examined by immunofluororescent staining with monoclonal antibodies 3E10-H10-F12 (ATCC HB-12564), 6F11-F8-C11 (ATCC HB-12565), and 3C2-E-7-F10 (ATCC HB-12566). Two assay methods were utilized: cell suspension method and fixed cell method.

In the cell suspension method, cells were cultured in RMPI 1640 (BioWhittaker) containing 10% fetal bovine serum (complete medium). To perform the assay, the cells were removed from the tissue culture flask with trypsin and then counted using trypan blue exclusion method. At least $4\times10^6$ cells were required for each assay. The cells were then centrifuged at 900 rpm at 4° C. for ten minutes, the supernatant discarded, and the cells resuspended in 2 ml complete medium. The cell suspension was equally divided into two centrifuge tubes and kept on ice. The cell suspension in one tube was saved as a control. Into the other tube, the primary antibody, i.e., a monoclonal antibody of the present invention, was added to a final concentration of 1 $\mu$g/ml to form a treated cell suspension. At this point the control cell suspension and the treated cell suspension were processed as follows. The cell suspensions were incubated at 4° C. for one hour, centrifuged as given above for ten minutes, the supernatant discarded, the cells resuspended in 5 ml ice cold Hank's Balanced Salt Solution without calcium or magnesium (BioWhittaker)(HBSS) and recentrifuged as given above, and the supernatant discarded. The cell suspensions were resuspended in 100–500 microliters of the secondary antibody, e.g., fluorescein-conjugated goat IgG fraction to mouse IgG (whole molecule) (Cappel, Durham, N.C.), diluted 1:100 in cold complete medium. After incubating at 4° C. for one hour, the cell suspensions were washed three times with cold HBSS and centrifuged as given above. After the final wash, the supernatant was discarded and the cells were resuspended in a minimum volume of complete medium to a final density of $5\times10^6$ cells/ml. The cell suspension was kept on ice until viewed on the fluorescence microscope.

In the fixed cell method, the cells were cultured in RMPI 1640 (BioWhittaker) containing 10% fetal bovine serum (complete medium) in Chamber Slide tissue culture chambers (Nalgene, Rochester, N.Y.) to about $1\times10^4$ cells/well. For the assay, the culture medium was then gently removed from the chamber well, or wells. A PBS wash was performed by adding 200 microliters of phosphate buffered saline (PBS) to each well, gently removing the PBS from the wells and discarding the PBS. This PBS wash was repeated once. Control wells were prepared by adding 100 microliters of complete medium. Treated wells were prepared by adding 100 microliters of complete medium containing the primary antibody, i.e., a monoclonal antibody of the present invention, up to a final concentration of 1 $\mu$g/ml. The control wells and treated wells were both processed as follows. The cells were incubated at 4° C. for one hour and washed three times in PBS as described above. To each well was added 100 microliters of the secondary antibody, e.g., fluorescein-conjugated goat IgG fraction to mouse IgG (whole molecule) (Cappel) diluted 1:100 in complete medium. The cells were incubated at 4° C. for one hour and then washed three times in PBS as given above. After removing the upper structure and gasket from each chamber slide, the slide was placed into a coplin staining jar containing acetone at −20° C. for one minute, removed from the staining jar, and let dry while standing on end. After removing any residual gasket pieces from the slide, small droplets of Vectashield mounting medium (Vector Laboratories, Burlington, N.C.) were dropped over the slide, and a coverslip was placed over the slide and pressure applied to remove any air bubbles present under the coverslip. The edges of the coverslip were sealed with a sealant such as fingernail polish, and the top and bottom surfaces of the slide were cleaned with alcohol before viewing on the fluorescence microscope.

For both immunofluorescence assays, the cells were examined on a fluorescence microscope for the presence of fluorescent material in association with the cells. The presence of fluorescence demonstrated a specific binding between the primary antibody and LCGA which is indicative of NSCLC cells, while the absence of fluorescence indicated the absence of LCGA and, hence, the absence of NSCLC cells. The results show a strong fluorescent signal for the NSCLC A549 cell line with all three monoclonal antibodies. This cell line was used to clone LCGA. The NSCLC cell line SKMES (of squamous cell origin) showed a weak/moderate signal with 3E10-H10 -F12 and 6F11-F8-C11 monoclonal antibodies. The staining for cancers of other origins were, for all three monoclonal antibodies, negative for melanoma (G361 and HT144 cell lines) and epidermoid cells (Hep-2); weak/moderate for colon (LoVo and HT-29) and either negative (BT-20) or weak/moderate (MCF 7) for breast. In contrast, two cell lines of ovarian origin were moderate/strong to strong (CaOV-3 and CaOV-4) for all three monoclonal antibodies. A third ovarian cancer cell line (SKOV-3) was weakly positive for all three monoclonal antibodies.

Patient samples were also examined for specific binding of the monoclonal antibodies generated from the hybridomas of the present invention to NSCLC cells. Example 1 presents studies in which specific binding was demonstrated between NSCLC cells and monoclonal antibody 6F11-F8-C11 (ATCC HB-12565) while normal tissue did not show significant reactivity.

The monoclonal antibodies of the present invention can be useful for the diagnosis of tumors expressing LCGA identified by the antibodies. For example, the monoclonal antibodies of the present invention can be used in in vitro diagnostic methods for determining the presence of a malignant condition in human lung tissue by examining a patient's lung tissue for presence of an antigen capable of reacting with one or more of the monoclonal antibodies. In one such method, the patient's lung tissue can be contacted with at least one monoclonal antibody of the present invention or a functional equivalent or fragment of this antibody which defines a determinant cite on the cell associate antigen LCGA, and any detected interaction of the antibody or antibody fragment and antigen determinants denotes the presence of the LCGA tumor marker and thus the presence of malignant disease in the lung tissue. One such method involves the determination of the presence of carcinoma cells in a specimen suspected of containing such cells. The specimen is contacted with the monoclonal antibody, which is capable of distinguishing such cells from other cell types which might be present in the specimen. The contact is carried out under conditions which promote the binding of the antibody to such cells. After contact, the presence or absence of a binding of the antibody to the cells in the specimen is determined. The binding is related to the presence or absence of carcinoma cells in this specimen. Generally, the specimen is contacted with a labeled specific binding partner of the monoclonal antibody. This label is capable of producing a detectable signal. Alternatively, the monoclonal antibody itself can be labeled. As exemplified herein, immunoperoxidase or immunofluorescence staining can be used; however any method known in the art for measuring the binding of antibody to antigen falls within the scope of this invention.

In addition, the monoclonal antibodies of the present invention can be useful for the diagnosis of ovarian tumors identified by the antibodies. For example, the monoclonal antibodies of the present invention can be used in in vitro diagnostic methods for determining the presence of a malignant condition in ovarian tissue by examining a patient's ovarian tissue for presence of an antigen capable of reacting with one or more of the monoclonal antibodies. In one such method, the patient's ovarian tissue can be contacted with at least one monoclonal antibody of the present invention or a functional equivalent or fragment of this antibody, and any detected interaction of the antibody or antibody fragment and antigen determinants denotes the presence of malignant disease in the ovarian tissue. One such method involves the determination of the presence of malignant ovarian cells in a specimen suspected of containing such cells. The specimen is contacted with the monoclonal antibody, which is capable of distinguishing such cells from other cell types which might be present in the specimen. The contact is carried out under conditions which promote the binding of the antibody to such cells. After contact, the presence or absence of a binding of the antibody to the cells in the specimen is determined. The binding is related to the presence or absence of carcinoma cells in this specimen. Generally, the specimen is contacted with a labeled specific binding partner of the monoclonal antibody. This label is capable of producing a detectable signal. Alternatively, the monoclonal antibody itself can be labeled. As exemplified herein, immunoperoxidase or immunofluorescence staining can be used; however any method known in the art for measuring the binding of antibody to antigen falls within the scope of this invention.

The antibodies of the present invention are also particularly suited for use in in vitro immunoassays to detect the presence of LCGA in body tissue, fluids, stools, or cellular extracts. In such immunoassays, the antibodies or antibody fragments can be utilized in liquid phase or bound to solid phase carrier. The antibodies or antibody fragments of the present invention can be labeled using any variety of labels and methods of labeling known to the art. Examples of types of labels which can be used in the present invention include, but are not limited to, enzyme labels, radioisotopic labels, nonradioactive labels, fluorescent labels, toxin labels, and chemoluminescent labels. The binding of these labels to antibodies or fragments thereof can be accomplished using standard techniques commonly known to those of ordinary skill in the art. (Harlow, E. and Lane, D. 1988. *Antibodies: A Laboratory Manual,* Cold Spring Harbor Laboratories, N.Y., pp. 319–358).

For example, antibodies or fragments of antibodies of the present invention can be used to quantitatively or qualitatively detect the presence of cells which express LCGA in histology samples and biopsies. Such detection can be accomplished using a variety of immunoassays. For example, by radioactively labeling the antibodies or antibody fragments, it is possible to detect LCGA through use of radioimmunoassays. Alternatively, fluorescent, enzyme, or other suitable labels can be employed. Detection of cells which express LCGA can be accomplished by removing a sample of tissue from a patient and then treating the sample with any suitable labeled antibody or antibody fragment of the present invention.

The monoclonal antibodies of the present invention can also be adapted for utilization in an immunometric assay also known as a two-site or sandwich assay. In a typical sandwich assay, a quantity of unlabeled antibody or fragment of antibody is bound to a solid support that is insoluble in the fluid being tested and a quantity of detectably labeled soluble antibody is added to permit detection and/or quantitation of the complex formed between the solid phase antibody, antigen and labeled antibody. (*Current Protocols in Immunology: Indirect Antibody-Sandwich ELISA to Detect Soluble Antigens.* 1991, John Wiley and Sons, New York, N.Y., pp. 2.0.1–2.1.18).

Another diagnostic method involves the in vivo localization of a tumor by administering to a patient a purified antibody or antibody fragment of the present invention labeled with an agent which gives a detectable signal. For example, the detection of cells which express LCGA can be accomplished by in vivo imaging techniques in which the labeled antibodies or fragments thereof are provided to a patient. The localization is then detected using external scintigraphy, emission tomography, or radio nuclear scanning. The presence of the lung carcinoma is detected without the prior removal of any tissue sample. This method can also provide better ways to stage cancer patients with respect to the extent of disease and to monitor changes in response to therapy.

The antibody or antibody fragments of the present invention can also be utilized in screening assays designed to detect and monitor LCGA in body fluids, including but not limited to, serum and other biological fluids such as sputum or bronchial affluxion at effective levels necessary for sensitive but accurate determinations. Example 2 provides an exemplary indirect ELISA assay which can be used as a screening assay for serum specimens.

The invention also has therapeutic applications. The monoclonal antibody of the present invention can be used to prepare a composition for treating tumors. The composition comprises therapeutically effective amounts of the antibody in association with a pharmaceutically acceptable vehicle. The antibody of the invention can also be used in immunoconjugates as a carrier of various agents which have an anti-tumor effect, including but not restricted to, chemotherapeutic drugs, toxins, immunological response modifiers, enzymes, and radioisotopes.

The ability to label antibodies or fragments of antibodies with toxin labels provides a method for treating lung cancer. In this embodiment, antibodies or fragments of antibodies which are capable of recognizing LCGA associated with such carcinoma are labeled with toxin molecules and administered to patients suspected of having such cancer. When such a toxin-derived molecule binds to a cancer cell, the toxin moiety will cause the death of the cancer cell.

EXAMPLE 1

Use of Monoclonal Antibody to Distinguish NSCLC Tissue from Normal Lung Tissue

The monoclonal antibody 6F11-F8-C11 (ATCC HB-12565) demonstrated specific binding to NSCLC (lung adenocarcinoma) cells but not to normal lung tissue.

Histologically normal human lung and lung adenocarcinoma tissues were obtained from surgical and autopsy specimens which were either frozen or in paraffin-embedded formalin-fixed blocks. All specimens were sectioned at five microns and placed on positively charged slides. The lung adenocarcinoma cell line A549 was used as a positive control. The murine monoclonal antibody 6F11-F8-C11 (ATCC HB-12565) stored at a stock concentration of 1.1 mg/ml and at 4–8° C. was diluted to a working concentration with Primary Antibody Diluent containing 2% bovine serum albumin (Research Genetics, Huntsville, Ala.) to form the test antibody solution. The optimum working concentration for the 6F11-F8-C11 monoclonal antibody was predetermined via an immunohistochemical staining titration analysis at serial dilutions of 1.25 µg/ml to 20 µg/ml antibody with A549 cells, normal lung sections and the negative control, wherein the optimum concentration (2.5 µg/ml) was that which provided the highest titer of antibody capable of detecting LCGA expressed in low levels without resulting in nonspecific binding. A murine IgG$_1$ isotype control (Sigma) was selected as a negative control antibody, and the stock concentration of 1.0 mg/ml stored at 4–8° C. was diluted to a working concentration equivalent to the working concentration of the test antibody solution with Primary Antibody Diluent containing 2% bovine serum albumin.

Immunohistochemical studies were performed using an indirect peroxidase-conjugated streptavidin methodology. For frozen tissue, cryostat sections were fixed in acetone at 4° C. for five minutes. To block endogenous peroxidase activity, tissue slides were treated with 3% hydrogen peroxide/PBS for 15 minutes and then repeatedly washed in PBS. To prevent nonspecific binding, tissue sections were treated with Avidin blocking solution (Vector Laboratories, Burlingame, Calif.) for fifteen minutes and biotin blocking solution (Vector Laboratories, Burlingame, Calif.) for fifteen minutes at room temperature. The tissue sections were then blocked with 5% normal horse serum in PBS (Jackson ImmunoResearch, West Grove, Pa.) for ten minutes. For negative control slides, the tissue sections were incubated with murine IgG$_1$ isotype control for 30 minutes at room temperature. For test samples and positive tissue control slides (A549), tissue sections were incubated with 2.5 µg/ml 6F11-F8-C11 monoclonal antibody for 30 minutes at room temperature. At this point all control slides, test samples, and positive tissue control samples were processed as follows. Tissue sections were washed in PBS and incubated with streptavidin peroxidase (Boehringer Mannheim, Indianapolis, Ind.) diluted 1:1000 in PBS for 20 minutes at room temperature and dipped in 0.1% Triton X-100 (Sigma) in PBS. To visualize the peroxidase reaction, the tissue sections were incubated with 3,3-diaminobenzidine-tetrahydrochloride (DAB) solution (Amresco, Solon, Ohio) containing hydrogen peroxide and urea (Sigma) for one to three minutes, washed thoroughly with tap water, counterstained with a modified Harris hematoxylin (Fisher), dipped in 0.25% acid alcohol, blued in 0.2% ammonia, dehydrated through graded alcohols, cleared in xylene, and coverslipped.

Fixed tissues were processed as described for frozen tissues with the exception that the tissue sections were subjected to a 0.025% trypsin pretreatment procedure for five minutes at room temperature rather than the initial five-minute acetone fixation step.

Table I presents immunoperoxidase staining of human cancer and normal lung tissues with the 6F11-F8-C11 (HB-12565) monoclonal antibody in which tissue preparation and staining were performed by methods well known in the art. In two separate studies, normal lung tissue did not stain, while 8 of 10 and 11 of 11 lung adenocarcinoma specimens stained positive in Study 1 and Study 2, respectively. Background staining of endothelial, smooth muscle, inflammatory and nerve cells was not detected. Weak staining of fibroblasts (+1) was identified in 3 of 9 specimens in Study 1 and 9 of 11 specimens in Study 2. Weak staining of stromal cells (+1) was seen in 6 of 10 specimens in Study 1 and 2 of 11 specimens in Study 2. Moderate staining of stromal cells (+2) was observed in 1 specimen in Study 1.

TABLE I

Immunoperoxidase Staining of Normal Lung Tissue and Lung Adenocarcinoma with 6F11-F8-C11 Monoclonal Antibody

| Tissue | Study # | Number of specimens | Number of Positive Specimens | Staining intensity +1 | +2 | +3 |
|---|---|---|---|---|---|---|
| Normal lung |  | 2 | 0/2 | 0 | 0 | 0 |
| Lung adenocarcinoma | 1 | 10 | 8 | 4 | 3 | 1 |
| Lung adenocarcinoma | 2 | 11 | 11 | 1 | 1 | 9 |

EXAMPLE 2

Monoclonal Antibodies Against LCGA Utilized in Indirect ELISA

Monoclonal antibodies of the present invention were used in an indirect double antibody sandwich ELISA assay for the detection of LCGA. The following assay was conducted for each monoclonal antibody/LCGA epitope combination, using an affinity purified rabbit polyclonal antibody against one of the LCGA epitopes of interest as the second antibody.

Using LCGA antigenic protein from which the mouse monoclonal antibody was produced as the test protein, a stock solution of the test protein was prepared at 1.9 μg/ml in phosphate buffered saline with sodium azide (PBSN) [per liter $H_2O$: 0.2 g KCL (2.7 mM); 0.2 g $KH_2PO_4$ (1.5 mM); 8.0 g NaCl (137 mM); 2.16 g $Na_2HPO_4.7H_2O$ (8 mM); and 0.5 g $NaN_3$ (0.05%), pH 7.2–7.4]/0.025%BSA and stored at 4° C. An affinity purified rabbit polyclonal antibody against LCGA was also produced and maintained at 4° C.

Mouse monoclonal antibody against the test protein was diluted to 10 μg/ml in PBSN at room temperature. Fifty microliters of the monoclonal antibody solution was added to each well in IMMULON® IV (Dynex Technologies, Chantilly, Va.) 96-well microtiter plates, the plates were sealed, and incubated overnight at room temperature.

Using a multi-channel pipettor to add and remove solutions, the plates were blocked from nonspecific binding by removing the monoclonal antibody solution from the wells; rinsing the wells twice with 50 μl phosphate buffered saline (PBS) [per liter $H_2O$: 0.2 g KCL (2.7 mM); 0.2 g $KH_2PO_4$ (1.5 mM); 8.0 g NaCl (137 mM); and 2.16 g $Na_2HPO_4.7H_2O$ (8 mM), pH 7.2–7.4]; adding to each well 380 μl borate blocking buffer (BB) [10.51 g $H_3BO_3$ (0.17 M); 7.01 g NaCl (0.12M); 0.5 ml Tween 20 (0.05%); 2 ml 500 mM EDTA (1 mM); 2.5 g bovine serum albumin (BSA) (0.25%); and 0.5 g $NaN_3$ (0.05%), pH 8.5] and incubating at room temperature for thirty minutes; removing borate blocking buffer and rinsing the wells twice with 380 μl PBS; adding to each well 380 μl of freshly prepared 5% nonfat dry milk in PBS (NFDM/PBS) (5 g nonfat dry milk in 100 ml PBS) and incubating at room temperature for thirty minutes; and removing NFDM/PBS and rinsing the wells twice with 380 μl PBS.

A working solution of the test protein was prepared by diluting the protein to 24 ng/ml by adding 25.26 μl of the 1.9 μg/ml stock solution to 1974.74 μl PBS/0.025% BSA. After making a series of 2X dilutions of the test protein working solution using PBS/0.025% BSA at room temperature, the various test protein dilutions were applied using a multi-channel pipettor to the blocked microtiter plates at 50 μl per well, and the plates were sealed and incubated at room temperature for two hours. Using a multi-channel pipettor to add and remove solutions, the test protein solutions were removed, and the plates were rinsed twice with 50 μl PBS. To each well was added 200 μl 2.5% NFDM/PBS (2.5 g nonfat dry milk in 100 ml PBS), and the plates were incubated at room temperature for ten minutes. The plates were rinsed twice with 200 μl PBS, removing the last traces of PBS with pipettor tips.

The affinity purified rabbit polyclonal antibody was diluted to 0.037 μg/ml in PBS/1% BSA. After adding 50 μl of the diluted polyclonal antibody to each microtiter well, the plates were covered and incubated at room temperature for two hours. Using a multi-channel pipettor to add and remove solutions, the polyclonal antibody was removed, and the plates were rinsed twice with 50 μl PBS. To each well was added 200 μl 12.5% NFDM/PBS (2.5 g nonfat dry milk in 100 ml PBS), and the plates were incubated at room temperature for ten minutes. The plates were rinsed twice with 200 μl PBS, removing the last traces of PBS with pipettor tips.

The antibody conjugate, i.e., antibody goat F(ab')2×rabbit IgG and IgL conjugated to horseradish peroxidase (BioSource International, Camarillo, Calif.) was diluted 1:16000 in PBS/1%BSA. After adding 50 μl of the diluted antibody conjugate to each well, the plates were covered and incubated at room temperature for two hours. Using a multi-channel pipettor to add and remove solutions, the antibody conjugate was removed, and the plates were rinsed twice with 50 μl PBS. To each well was added 200 μl 2.5% NFDM/PBS (2.5 g nonfat dry milk in 100 ml PBS), and the plates were incubated at room temperature for ten minutes. The plates were rinsed twice with 200 μl PBS, removing the last traces of PBS with pipettor tips.

Fifteen minutes before using, the peroxidase substrate was prepared as follows. Phosphate-citrate buffer with sodium perborate (Sigma; Catalog No. P4922) was prepared by dissolving one capsule in 100 ml deionized water to yield 0.05M buffer containing 0.03% sodium perborate, pH 5.0 at 25° C. Per microtiter plate, one 3,3',5,5'-tetramethylbenzidine (TMB) tablet (Sigma; Catalog No. T3405) was dissolved into 10 ml phosphate-citrate/sodium perborate buffer, and the solution was filtered through a 0.22 μm syringe filter.

To detect the presence of bound antibody conjugate in the microtiter plates, 100 μl peroxidase substrate was added per well. The microtiter plates were covered and stored in a dark place at room temperature. After one hour, 50 μl 1M $H_2SO_4$ stopping solution was added per well. A color change from blue to yellow, indicating the presence of bound antibody conjugate, was read using a microtiter plate reader (Molecular Devices Corp., Menlo Park, Calif.) at 450/650 nm.

Figure 1:
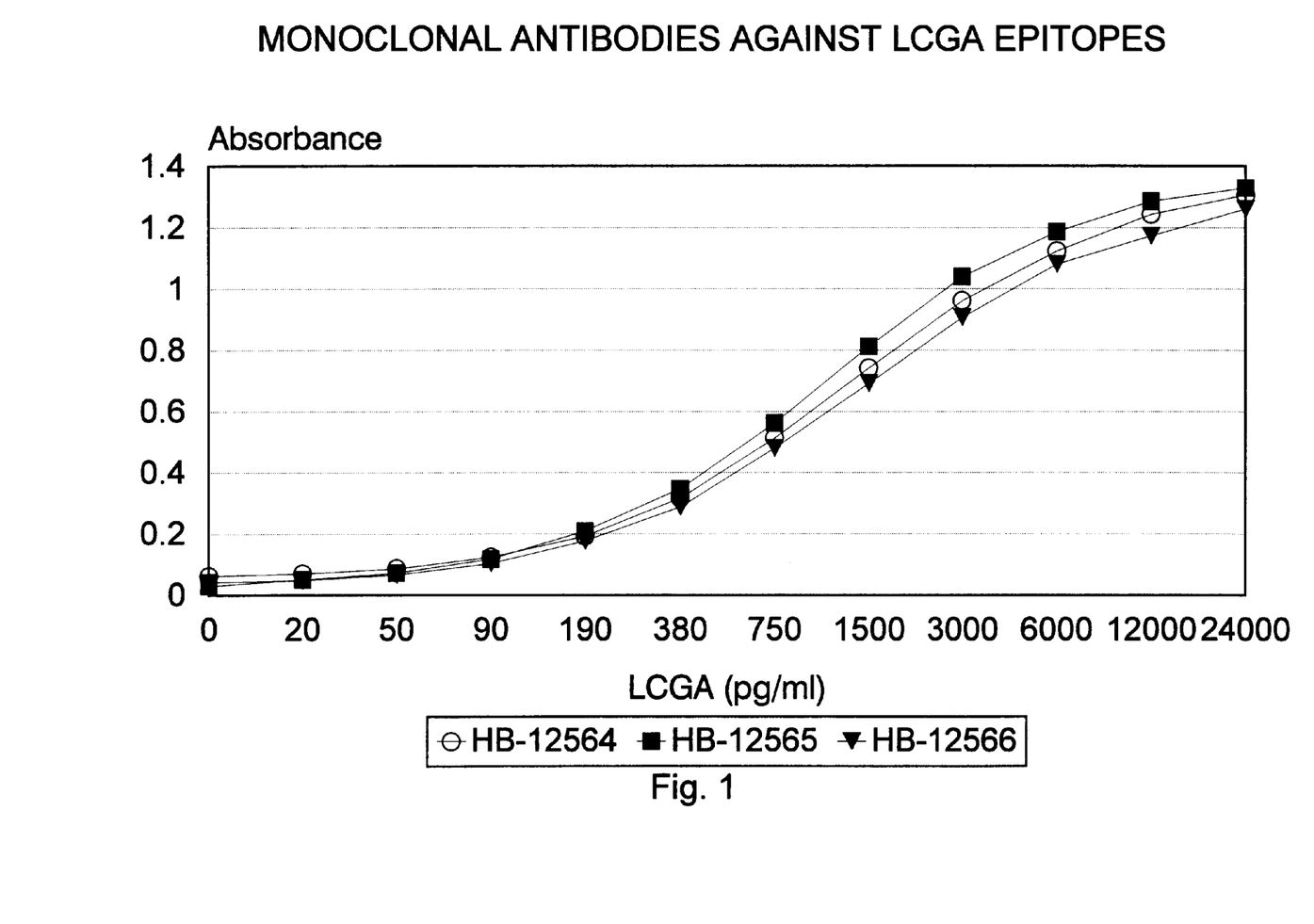
FIG. 1 is a graph depicting reaction of monoclonal antibodies against LCGA.

The results of the assay are presented in Table II and FIG. 1. With this assay, all three monoclonal antibodies were capable of detecting the presence of LCGA. The level of detection of LCGA for 3E10-H10-F12 (ATCC HB-12564) and 3C2-E7-F10 (ATCC HB-12566) was 90 pg/ml and for 6F11-F8-C11 (ATCC HB-12565) was 50 pg/ml.

TABLE II

Monoclonal Antibodies Against LCGA as Coating Protein for Indirect ELISA

| LCGA Concentration (pg/ml) | Absorbance (Mean Value) | | |
|---|---|---|---|
| | 3E10-H10-F12 (ATCC HB-12564) | 6F11-F8-C11 (ATCC HB-12565) | 3C2-E-7-F10 (ATCC HB-12566) |
| 24000 | 1.306 ± 0.008 | 1.329 ± 0.009 | 1.261 ± 0.032 |
| 12000 | 1.243 ± 0.014 | 1.286 ± 0.009 | 1.173 ± 0.023 |
| 6000 | 1.124 ± 0.015 | 1.187 ± 0.012 | 1.081 ± 0.034 |
| 3000 | 0.962 ± 0.0100 | 0.040 ± 0.014 | 0.907 ± 0.034 |
| 1500 | 0.742 ± 0.008 | 0.813 ± 0.011 | 0.692 ± 0.014 |
| 750 | 0.513 ± 0.002 | 0.562 ± 0.011 | 0.480 ± 0.019 |
| 380 | 0.317 ± 0.007 | 0.347 ± 0.007 | 0.288 ± 0.004 |
| 190 | 0.192 ± 0.002 | 0.209 ± 0.005 | 0.177 ± 0.005 |
| 90 | 0.124 ± 0.003 | 0.118 ± 0.001 | 0.104 ± 0.001 |
| 50 | 0.087 ± 0.002 | 0.073 ± 0.004 | 0.067 ± 0.001 |
| 20 | 0.070 ± 0.002 | 0.051 ± 0.003 | 0.048 ± 0.002 |
| 0 | 0.063 ± 0.015 | 0.030 ± 0.009 | 0.042 ± 0.011 |

We claim:

1. A monoclonal antibody, an antigen binding fragment or recombinant binding protein thereof which is specific for a non-small cell lung carcinoma cell antigen having the epitope binding specificity of an antibody produced by hybridoma cell line 3E10-H10-F12 designated as ATCC HB-12564.

2. The monoclonal antibody of claim 1, wherein said antibody is secreted by said hybridoma cell line 3E10-H10-F12 designated as ATCC HB-12564.

3. The antigen binding fragment of claim 1, wherein said fragment is derived from said antibody secreted by said hybridoma cell line 3E10-H10-F12 designated as ATCC HB-12564.

4. The recombinant binding protein of claim 1, wherein said protein is a recombinant protein comprising a variable region of an antibody secreted by said hybridoma cell line.

5. The monoclonal antibody, antigen binding fragment or recombinant binding protein of claim 1, wherein said antibody, antigen binding fragment or recombinant binding protein specifically binds to amino acids 173 through 179 of SEQ ID NO:2 or a portion thereof.

6. A hybridoma cell line which produces the monoclonal antibody of claim 1.

7. A hybridoma cell line which produces the monoclonal antibody of claim 2.

8. A composition comprising said monoclonal antibody, said antigen binding fragment or said recombinant binding protein of claim 1, wherein said monoclonal antibody, said antigen binding fragment or said recombinant binding protein specifically binds amino acids 173 through 179 of SEQ ID NO:2 or a portion thereof or has the epitope binding specificity of an antibody produced by hybridoma cell line 3E10-H10-F12 designated as ATCC HB-12564.

9. A composition comprising an isolated human monoclonal antibody, wherein said antibody specifically binds amino acids 173 through 179 of SEQ ID NO:2 or a portion thereof or has the epitope binding specificity of an antibody produced by hybridoma cell line 3E10-H10-F12 designated as ATCC HB-12564.

10. A composition comprising a humanized antibody, wherein said antibody specifically binds amino acids 173 through 179 of SEQ ID NO:2 or a portion thereof or has the epitope binding specificity of an antibody produced by hybridoma cell line 3E10-H10-F12 designated as ATCC HB--12564.

11. An isolated antibody, wherein said antibody specifically binds amino acids 173 through 179 of SEQ ID NO:2 or a portion thereof or has the epitope binding specificity of an antibody produced by hybridoma cell line 3E10-H10-F12 designated as ATCC HB-12564.

12. A monoclonal antibody, an antigen binding fragment or recombinant binding protein thereof which is specific for a non-small cell lung carcinoma cell antigen having the epitope binding specificity of an antibody produced by hybridoma cell line 6F11-F8-C11 designated as ATCC HB-12565.

13. The monoclonal antibody of claim 12, wherein said antibody is secreted by said hybridoma cell line 6F11-F8-C11 designated as ATCC HB-12565.

14. The antigen binding fragment of claim 12, wherein said fragment is derived from said antibody secreted by said hybridoma cell line 6F11-F8-C11 designated as ATCC HB-12565.

15. The recombinant binding protein of claim 12, wherein said protein is a recombinant protein comprising a variable region of an antibody secreted by said hybridoma cell line.

16. The monoclonal antibody, antigen binding fragment or recombinant binding protein of claim 12, wherein said antibody, antigen binding fragment or recombinant binding protein specifically binds to amino acids 209 through 215 of SEQ ID NO:2 or a portion thereof.

17. A hybridoma cell line which produces the monoclonal antibody of claim 12.

18. A hybridoma cell line which produces the monoclonal antibody of claim 13.

19. A composition comprising said monoclonal antibody, said antigen binding fragment or said recombinant binding protein of claim 12, wherein said a monoclonal antibody, said antigen binding fragment or said recombinant binding protein specifically binds amino acids 209 through 215 of SEQ ID NO:2 or a portion thereof or has the epitope binding specificity of an antibody produced by hybridoma cell line 6F11-F8-C11 designated as ATCC HB-12565.

20. A composition comprising an isolated human monoclonal antibody, wherein said antibody specifically binds amino acids 209 through 215 of SEQ ID NO:2 or a portion thereof or has the epitope binding specificity of an antibody produced by hybridoma cell line 6F11-F8-C11 designated as ATCC HB-12565.

21. A composition comprising a humanized antibody, wherein said antibody specifically binds amino acids 209 through 215 of SEQ ID NO:2 or a portion thereof or has the epitope binding specificity of an antibody produced by hybridoma cell line 6F11-F8-C11 designated as ATCC HB-12565.

22. An isolated antibody, wherein said antibody specifically binds amino acids 209 through 215 of SEQ ID NO:2 or a portion thereof or has the epitope binding specificity of an antibody produced by hybridoma cell line 6F11-F8-C11 designated as ATCC HB-12565.

23. A monoclonal antibody, an antigen binding fragment or recombinant binding protein thereof which is specific for a non-small cell lung carcinoma cell antigen having the epitope binding specificity of an antibody produced by hybridoma cell line 3C2-E7-F10 designated as ATCC HB-12566.

24. The monoclonal antibody of claim 23, wherein said antibody is secreted by said hybridoma cell line 3C2-E7-F10 designated as ATCC HB-12566.

25. The antigen binding fragment of claim 23, wherein said fragment is derived from said antibody secreted by said hybridoma cell line 3C2-E7-F10 designated as ATCC HB-12566.

26. The recombinant binding protein of claim 23, wherein said protein is a recombinant protein comprising a variable region of an antibody secreted by said hybridoma cell line.

27. A hybridoma cell line which produces the monoclonal antibody of claim 23.

28. A hybridoma cell line which produces the monoclonal antibody of claim 24.

29. A composition comprising said monoclonal antibody, said antigen binding fragment or said recombinant binding protein of claim 23, wherein said monoclonal antibody, said antigen binding fragment or said recombinant binding protein has the epitope binding specificity of an antibody produced by hybridoma cell line 3C2-E7-F10 designated as ATCC HB-12566.

30. A composition comprising an isolated human monoclonal antibody, wherein said antibody has the epitope binding specificity of an antibody produced by hybridoma cell line 3C2-E7-F10 designated as ATCC HB-12566.

31. A composition comprising a humanized antibody, wherein said antibody has the epitope binding specificity of an antibody produced by hybridoma cell line 3C2-E7-F10 designated as ATCC HB-12566.

32. An isolated antibody, wherein said antibody has the epitope binding specificity of an antibody produced by hybridoma cell line 3C2-E7-F10 designated as ATCC HB-12566.

* * * * *

UNITED STATES PATENT AND TRADEMARK OFFICE
CERTIFICATE OF CORRECTION

PATENT NO : 6,117,981
DATED : September 12, 2000
INVENTOR(S): Richard M. Torczynski, et al.

It is certified that error appears in the above-identified patent and that said Letters Patent are hereby corrected as shown below:

Col. 6, line 13, after "for", change "a epitoped" to "epitopes".

Col. 9, line 29, after "determinant", change "cite" to "site".

Col. 10, line 66, after "or", change "radio nuclear" to "radionuclear".

Col. 20, Claim 10, line 41, change "HB--12564" to "HB-12564".

Signed and Sealed this

Twenty-fourth Day of April, 2001

Attest:

NICHOLAS P. GODICI

Attesting Officer

Acting Director of the United States Patent and Trademark Office